(12) United States Patent
Palefsky et al.

(10) Patent No.: US 8,859,618 B2
(45) Date of Patent: Oct. 14, 2014

(54) SILICONE GEL-BASED COMPOSITIONS FOR WOUND HEALING AND SCAR REDUCTION

(71) Applicant: Valeant Pharmaceuticals International, Bridgewater, NJ (US)

(72) Inventors: Irwin Palefsky, Plainview, NY (US); Ni'Kita Wilson, Union, NJ (US)

(73) Assignee: Valeant Pharmaceuticals International, Bridgewater, NJ (US)

( * ) Notice: Subject to any disclaimer, the term of this patent is extended or adjusted under 35 U.S.C. 154(b) by 0 days.

(21) Appl. No.: 14/031,303

(22) Filed: Sep. 19, 2013

(65) Prior Publication Data

US 2014/0023610 A1    Jan. 23, 2014

Related U.S. Application Data

(62) Division of application No. 12/242,681, filed on Sep. 30, 2008, now Pat. No. 8,563,604.

(60) Provisional application No. 60/997,166, filed on Sep. 30, 2007.

(51) Int. Cl.

| | | |
|---|---|---|
| A61K 31/34 | (2006.01) |
| A61K 31/695 | (2006.01) |
| A61K 31/74 | (2006.01) |
| A61K 8/89 | (2006.01) |
| A61L 26/00 | (2006.01) |
| A61L 15/22 | (2006.01) |
| C08L 83/04 | (2006.01) |
| A61L 15/60 | (2006.01) |
| C08G 77/00 | (2006.01) |
| C08G 77/46 | (2006.01) |
| C08G 77/50 | (2006.01) |

(52) U.S. Cl.
CPC ......... A61L 26/0052 (2013.01); A61L 26/0019 (2013.01); *C08G 77/70* (2013.01); A61L 15/225 (2013.01); *A61L 2300/428* (2013.01); A61L 26/0066 (2013.01); C08L 83/04 (2013.01); A61L 15/60 (2013.01); *C08G 77/46* (2013.01); *C08G 77/50* (2013.01)
USPC ........................... 514/474; 424/78.06; 514/63

(58) Field of Classification Search
CPC ............ A61L 26/0019; A61L 26/0052; A61L 2300/428; C08L 83/04; C08L 83/00; C08G 77/70; C08G 77/50; A61K 8/676; A61K 8/89; A61K 8/891; A61K 2800/436; A61K 2800/437
See application file for complete search history.

(56) References Cited

U.S. PATENT DOCUMENTS

| | | | |
|---|---|---|---|
| 5,741,509 A | 4/1998 | Kushner | |
| 8,563,604 B2 | 10/2013 | Palefsky et al. | |
| 2005/0100568 A1* | 5/2005 | De Mul et al. ................ | 424/401 |

FOREIGN PATENT DOCUMENTS

| | | |
|---|---|---|
| JP | 2003-40756 A | 2/2003 |
| JP | 2005-29524 A | 2/2005 |
| WO | WO 01/23011 A1 | 4/2001 |
| WO | WO 2004/006972 | 1/2004 |
| WO | WO 2004006972 A1 * | 1/2004 |

OTHER PUBLICATIONS

Borgognoni, "Biological effects of silicone gel sheeting," *Wound Repair Regen.* 10(2):118-121 (2002).
Chan et al., "A randomized, placebo-controlled, double-blind, prospective clinical trial of silicone gel in prevention of hypertrophic scar development in median sternotomy wound," *Plast. Reconstr. Surg.* 116(4):1013-1020; discussion 1021-1022 (2005).
Chernoff et al., "The efficacy of topical silicone gel elastomers in the treatment of hypertrophic scars, keloid scars, and post-laser exfoliation erythema," *Aesth. Plast. Surg.* 31(5):495-500 (2007).
Fonseca Capdevila et al., "Prevención de secuelas cicatrizales de la extirpación de lesiones cutáneas benignas: estudio multicéntrico, prospective, abierto y controlado que compara un gel de silicona y láminas de silicona en 131 pacientes con nevos melanocíticos," ("Prevention of scar sequels after excision of benign cutaneous lesions: multicenter, prospective, open label, controlled study comparing a silicone gel versus silicone sheets in 131 patients with melanocytic nevi") *Piel* 22:421-426 (2007).
Leventhal et al., "Treatment of keloids and hypertrophic scars: a meta-analysis and review of the literature," *Arch. Facial Plast. Sura.* 8(6):362-368 (2006).
Lund and Crandon, "Ascorbic Acid and Human Wound Healing," *Ann. Surg.* 114(4):776-790 (1941).
Murison and James, "Preliminary evaluation of the efficacy of Dermatix silicone gel in the reduction of scar elevation and pigmentation," *J. Plast. Reconstr. Aesthet. Surg.* 59(4):437-439 (2006).
Reid et al., "Reduction of hypertrophic scar via retroviral delivery of a dominant negative TGF-β receptor II," *J. Plast. Reconstr. Aesthet. Surg.* 60(1):64-72 (2007); discussion 73-74.
Sepehrmanesh, M., "Observational study of 1,522 patients using Dermatix gel," *Kompendium Dermatologie* 1:30-32 (2006).

(Continued)

*Primary Examiner* — Daniel Sullivan
*Assistant Examiner* — Peter Anthopolos
(74) *Attorney, Agent, or Firm* — Toan P. Vo; Timothy J. Shea, Jr.; Mattew S. Bodenstein

(57) ABSTRACT

This invention is a composition comprising a cyclic siloxane, a silicone occlusive fluid, a silicone occlusive gel, and a silicone resin powder. The composition is useful for wound healing.

17 Claims, 2 Drawing Sheets

(56) References Cited

OTHER PUBLICATIONS

Signorini and Clementoni, "Clinical evaluation of a new self-drying silicone gel in the treatment of scars: a preliminary report," *Aesth. Plast. Surg.* 31(2):183-187 (2007).
English Language Translation of Japanese Patent Application Publication No. JP 2003-40756 A.
Non-Final Rejection, mailed Feb. 16, 2011, in U.S. Appl. No. 12/242,681, filed Sep. 30, 2008.
Non-Final Rejection, mailed Mar. 28, 2011, in U.S. Appl. No. 12/242,681, filed Sep. 30, 2008.
Final Rejection, mailed Mar. 28, 2012, in U.S. Appl. No. 12/242,681, filed Sep. 30, 2008.
Notice of Allowance, mailed Jun. 21, 2013, in U.S. Appl. No. 12/242,681, filed Sep. 30, 2008.
International Search Report, mailed Jan. 13, 2010, in PCT/US2008/078340, filed Sep. 30, 2008.

* cited by examiner

SILICONE GEL-BASED COMPOSITIONS FOR WOUND HEALING AND SCAR REDUCTION

This application claims priority under 35 U.S.C. §119(e) to U.S. Provisional application Ser. No. 60/997,166, filed Sep. 30, 2007, the entire contents of which is incorporated herein by reference.

TECHNICAL FIELD

The present invention relates to compositions containing various silicone compounds, which are suitable for promoting the healing of skin wounds and for the prevention of scarring.

BACKGROUND OF THE INVENTION

Significant skin wounds, such as are caused by injury or surgery, frequently lead to scarring. Scarring in many instances results in a diminished sense of touch, loss of flexibility and loss of range of motion (where scars run across joints). Scarring also results in obvious cosmetic problems, particularly when on the face and hands. Skin wounds are also pane to infection, and even with conventional dressings, infections are fairly common. Burn victims are particularly susceptible to infections, and can be left with severe scarring when the wounds heal. There is a need for methods of treatment of skin injuries that minimize or eliminate scar formation.

Conventional wound dressings, such as are made from cotton gauze and various polymers, leave much to be desired, especially when a large area of skin must be dressed. The ability of the dressing to remain in place and protect the wound becomes progressively more compromised as the area of the wound increases, while at the same time the removal the dressing without injury to the underlying tissue becomes progressively more difficult. Wound dressings must stretch and flex to accommodate the movement of muscles and joints; this too gets more difficult as the dressing gets larger, in the case of facial dressings, it is desirable to minimize the visual impact of the dressing, and this of course rapidly becomes impossible as the size of the wound increases. Finally, conventional wound dressings require frequent changing, which is particularly costly in a hospital setting where the time value of professional staff, and the costs of disposing of medical waste, are significant. There is a need for improved wound dressings that do not have these disadvantages.

To address these needs, a number of products have been developed and marketed (Reviews; L. Borgognoni, *Wound Repair and Regeneration* (2002), 10:118-121; D. Leventhal at al., *Arch Facial Plast Surg* (2006), 8:362-368). Among the more successful are silicone gel sheets ("SGS") and silicone gel ointments, and combinations thereof. The use of these silicone-based polymers and gels has been proven to reduce the appearance of scars when used consistently for sufficiently extended periods of time. (Chan, K Y, et al., *Plast Reconstr Surg.* (2005), 116:1013-1020; Signorini M, Clementonil M T., *Aesthetic Plast Surg.* (2007), 31; 183-187; Chernoff W G, et al., *Aesthetic Plast Surg.* (2007) 31:495-500; Fonseca Capdevila E, at al., *Piel* (2007) (in press); Sepehrmanesh M., *Kompendium Dermatologie* (2006), 1:30-32; Murison M, James W., *J Plast Reconstr Aesthet Surg.* (2006), 59:437-439.)

It is impractical to use sheeting on large areas and near joints, and it cannot be used easily on, the face and other areas where the contours or motility of the skin make it difficult to ensure adequate contact and coverage. Taping is often needed to secure the sheeting to the skin. Also, patients may be reluctant to use the sheeting on unclothed areas during the day, making compliance with treatment a concern. Finally, the sheets must be washed frequently to prevent complications such as rashes and infection.

Although the mechanism by which silicone sheets and polymers reduce the appearance of scars is not presently known, it has been hypothesized that the silicone provides a barrier function that somehow promotes the healing process. This may involve increased hydration, pH control, increased temperature, and control of oxygen tension. The presence of unspecified silicone compounds in the healing skin have been proposed to somehow limit scar formation. Commercial products formed from silicone-based polymers and specifically targeting wound healing and the treatment of existing scars are presently available. Specific examples of such commercial products include Neosporin Scar Solutions™ sheets, Cica-Care™ sheets, Mepiform™ scar dressings, and Dermatix™ silicone gel.

Silicone polymer gel compositions for wound treatment have been described (see for example U.S. Pat. No. 5,741, 509). Although the silicone-based polymers are effective in reducing the appearance of scars, the known compositions must be applied to the scars for long periods of time in order to achieve noticeable results. In particular, the silicone-based polymer gels are typically worn on the scars far about 18 hours per day, every day, for several months. Significant discomfort may result from the long periods during which the silicone-based polymers must be worn on the scar. Also, the typical gel, is a viscous material that leaves a relatively thick layer on the skin, which is at best imperfectly camouflaged with makeup. Although the layer of silicone can be rendered nearly invisible with suitably sophisticated cosmetic materials and methods, few patients have the time and resources to use these methods or to employ a professional cosmetologist. The resulting impairment of physical appearance can discourage patient compliance with the rigorous and unusually lengthy treatment protocol. There is a need for an effective silicone polymer composition that is more comfortable, less visible, and more easily rendered inconspicuous by ordinary cosmetics.

BRIEF DESCRIPTION OF THE INVENTION

The invention provides a topically-applied silicone fluid that dries to a thin film on the skin. The compositions of the invention reduce the formation of overgrown scars (hypertrophic scars and keloids) after surgical incisions or accidental wounds, and reduce the size and improve the appearance of established overgrown scars. The compositions of the invention contain a cyclic siloxane as a base fluid with excellent spreading properties that is compatible with a wide range of other cosmetic ingredients. The compositions of the invention are relatively non-viscous, and are easily spread out into thin, uniform coating. The presence of a cyclic siloxane also imparts a soft silk feel to the skin, and the compositions of the invention are non-greasy and leave no oily residue or buildup.

DETAILED DESCRIPTION OR THE INVENTION

Figure 1A:
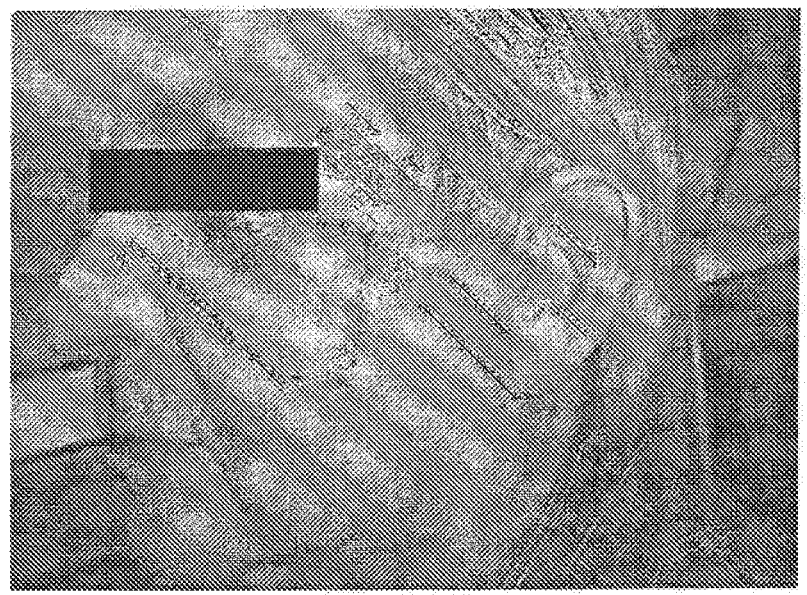
FIG. 1: Before (A) and after (B) photographs of a patient treated with a silicone gel composition of the present invention.

The compositions of the invention comprise a cyclic siloxane, a silicone occlusive fluid, a silicone occlusive gel, and a silicone resin powder. In preferred embodiments, the compositions further comprise an ascorbic acid fatty acid ester or salt thereof.

The functions of the components are thought to be as follows, but it should be understood that the invention is in no way limited in scope to these particular mechanisms of action: The cyclic siloxane provides fluidity and a smooth and pleasant texture, enabling the convenient application of a thin film over as wide an area as necessary. It may also serve as an emollient. The cyclic siloxane is volatile, and evaporates after application to leave the remaining components in the form of a thin occlusive film on the skin. The occlusive fluid and gel components are non-volatile hydrophobic materials that provide a flexible, biocompatible moisture barrier that is adhesive to the skin, emollient, non-irritating and non-toxic. The silicone resin powder is a film-forming agent which confers suitable rheological and tactile properties to the composition, ensuring that the barrier produced upon evaporation of the cyclic siloxane has a relatively dry, smooth feel. The non-volatile silicone components work together to generate a thin film protective barrier that is especially useful in areas of the body that are difficult to cover due to mobility/stretching of the skin, for example, around joints and on the face, as well as parts of the body with irregular shape. The resultant film that forms after evaporation of the cyclic siloxane is flexible, waterproof, yet gas permeable. The ascorbate ester is absorbed by the endothelial cell and cleaved in vivo to ascorbate, which provides an anti-oxidant function and is believed to promote normal collagen synthesis.

The cyclic siloxanes are of the formula

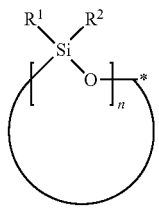

where n=4-6, and $R^1$ and $R^2$ are, in each incidence, independently H or $C_1$-$C_3$ alkyl. Suitable cyclic siloxanes include, but are not limited to, permethylated cyclic siloxanes, which are preferably selected from among the commercially-available materials cyclotetrasiloxane (octamethyloyclotetrasiloxane), cyclopentasiloxane (decamethylcycloperitasiloxane), and cyclehexasiloxane (doclecamethylcyclohexasiloxane), and mixtures thereof. In the most preferred embodiments, the cyclic siloxane is cyclopentasiloxane.

The cyclic siloxane constitutes between about 30-80% by weight of the compositions of the invention, preferably between about 45-65%, more preferably between about 55-65%.

The silicone occlusve fluid is a polyalkylsiloxane having a viscosity between about 50 cSt and 500 cSt, preferably between about 100 to 350 cSt. Suitable polyalkysiloxanes include, but are not limited to, poly(dimethylsiloxane), poly(methylethylsiloxane), poly(methylphenylsiloxane), and mixtures thereof. Particularly preferred is polydimethylsiloxane having a viscosity of about 200 cSt. The silicone occlusive fluid constitutes between about 1-15% by weight of the compositions of the invention, preferably between about 2-10%, and more preferably between about 3-7%.

The silicone occlusive gel is a dispersion of a silicone elastomer in a silicone oil. Particularly suitable elastomers are crosslinked silicone polymers having an average molecular weight in excess of 100,000 (e.g., between about 100,000 and 10,000,000). Suitable examples include, but are not limited to, crosslinked siloxanes (e.g., crosslinked dimethicone or dimethicone derivatives), copolymers such as stearyl methyldimethyl siloxane copolymer, polysilicone-11 (a crosslinked silicone rubber formed by the reaction of vinyl terminated silicone and (methylhydro dimethyl)polysiloxane in the presence of cyclomethicone), cetearyl dimethicone/vinyl dimethicone crosspolymer (a copolymer of cetearyl dimethicone crosslinked with vinyl dimethyl polysiloxane crosslinked with phenyl vinyl dimethylsiloxane), and dimethicone/vinyl dimethicone crosspolymer (a copolymer of dimethylpolysiloxane crosslinked with vinyl dimethylsiloxane). Preferred compositions of the invention comprise polysilicone-11.

The silicone oil dispersant may be any silicone liquid capable of dispersing the elastomer. Preferably it is a non-volatile silicone fluid. Suitable examples include, but are not limited to, dimethicone, phenyl trimethicone, phenyl dimethicone, dimethicone copolyol, and alkyl dimethicone copolyol. Preferably, the occlusive gel is a dispersion of polysilicone-11 in phenyltrimethicone. The occlusive gel comprises between about 10-60% by weight of the compositions of the invention, preferably between about 20-50%, and more preferably between about 30-40%. The silicone elastomer, in conjunction with the silicone occlusive fluid, provide favorable elasticity to the final film formed on the scar. This is especially beneficial at joints and on the face where the skin is particularly mobile.

The silicone resin powder may be one of the many film-forming silicone resins known in the cosmetic arts. Silsesquioxanes, approximately represented by the average formula $(R_3SiO_{3/2})_x$, are particularly suitable. Silsesquioxanes, typically prepared by partial hydrolysis of alkoxy- and haloalkylsilane precursors, are structurally ill-defined, insoluble cross-linked materials, comprised of a combination of $R_3SiO\text{—}$, $\text{—}OSiR_2O\text{—}$, and $RSi(O\text{—})_3$ monomer units. The R groups are generally methyl groups, but may be replaced in part by lower alkyl, vinyl, and phenyl groups in order to modify the physical properties of the polymer. Polymethylsilsequioxanes ($R\text{=}CH_3$) having a particle site of 4-8 μm are preferred for use in the present invention. The silicone resin powder comprises between about 1-10% by weight of the compositions of the invention, preferably between about 1-5%, and more preferably between about 2-3%. In addition to the theological and tactile properties imparted by the addition of the silicone resin powder, the silsequioxanes are capable of dispersing additional materials in cosmetic compositions, such as pigments.

Ascorbic acid fatty acid esters are ascorbic acid acylated with single or multiple fatty acid groups, wherein the fatty acids typically have 8 to 24 carbon atoms, and their salts. A variety of tetra($C_8$-$C_{24}$ acyl)ascorbic acids, and salts thereof, are commercially available. The more oxidation-resistant saturated fatty acid esters of ascorbic acid are preferred, including, but not limited to, ascorbyl laurate, ascorbyl myristate, ascorbyl palmiatate, ascorbyl isopalmitate, ascorbyl stearate, and ascorbyl behenate, and their salts, e.g., magnesium ascorbyl stearate. Ascorbic acid tetraisopalmitate is particularly preferred. The esters may be prepared using hydrogenated natural oils or fats, or fractions thereof, and accordingly may contain small amounts of various mixed esters in addition to that corresponding to the nominal identity of the material. Ascorbyl stearate prepared from canola oil, for example, commonly contains about 4% palmitate residues. The ascorbate ester is an optional component, but is preferably present in the compositions of the invention. The amount of ascorbate ester can be between about 0.1 and 2% by weight of the composition, in some embodiments between about 0.2 and 1%, and in still other embodiments, between about 0.3 and 0.7%. As an optional ingredient, the ascorbate ester can also be present in any amount between about 0 and 0.1% by weight, in addition to up to about 2% by weight. Therefore, the ascorbic acid ester or salt thereof can present in between about 0.01 and 2% by weight, for example. One skilled in the art will recognize the beneficial antioxidant effects of vitamin C, especially as it relates to wound healing. See for example, Lund, C. C.; Crandon, J. H. "Ascorbic Acid and Human Wound Healing," Annals of Surgery, 1941, 776-790.

EXAMPLES

1. Preparation of Exemplary Composition

Example 1

A mixture of cyclopentasiloxane (585 g), phenyltrimethicone dispersion of polysilicone-11 (Gransil™ PM--Gel) (350 g) and polydimethylsiloxane 200 cSt (40 g) is stirred and heated slowly to 50° C. While the heating is in progress, polymethysilsequioxane powder, 4-8 μm (Tospearl™ 2000B) (25 g) is added, followed by ascorbyl tetraisopalmitate (0.5 g). The mixture is stirred at 50° C. until homogenous, then cooled to room temperature.

2. In Vivo Testing

Rabbit Ear Model

Using a dermal biopsy punch and a dissecting microscope, 7-mm wounds were made on the ventral surface of each ear of four 3-kg New Zealand White rabbits (6 wounds on each ear). The wounds involved complete removal of the epithelium, dermis, and perichondrium. The wounds were covered with a polyurethane film until healing was complete (17 days).

The wounds on one ear were then treated once daily for 18 days by topically application of the silicone gel composition of Example 1. The six wounds on the other ear served as untreated controls. The animals were sacrificed on day 36 of the experiment.

Scar tissue was harvested, bisected at the highest point of the scar, and processed for histological analysis using hematoxylin and eosin staining. An observer blinded to the treatment quantified scar elevation by measuring the "scar elevation index" under 100× magnification. The scar elevation index was calculated as the area of the scar dermis (S) divided by the normal area of dermis (N), the latter being based on the height of the dermis in adjacent, unwounded skin (R. Reid et al., *J Plast Reconstr Aesthet Surg.* (2006), 60:64-72).

The mean scar elevation index in the control animals (N=20) was 1.68, and the mean scar elevation index in the treated animals (N=19) was 1.40 (p=0.007 vs. control, independent samples t-test).

3. Clinical Results

Figure 1B:
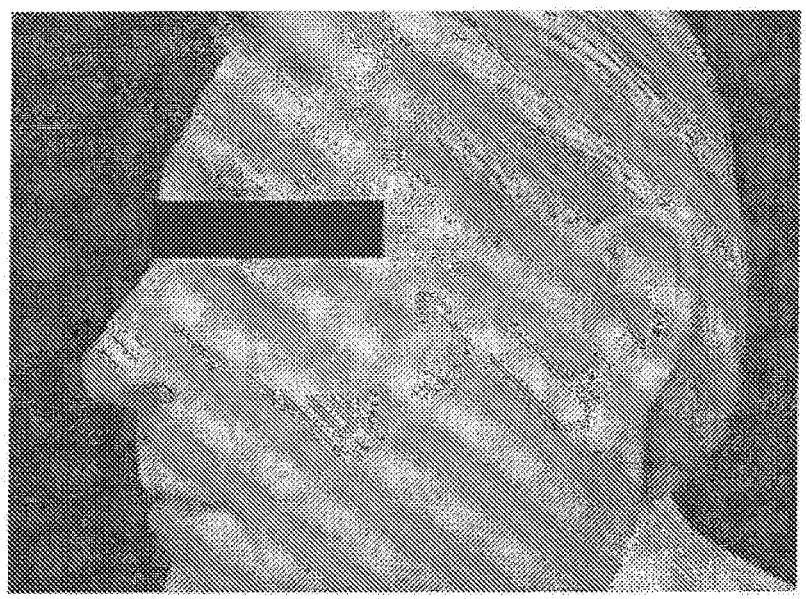

Application daily for two months to a large surgical facial scar resulted in substantial reduction in the amount and visibility of scar tissue (FIG. 1).

What is claimed:

1. A method for the treatment of wounds to reduce scarring comprising administering to a patient in need thereof an effective amount of a composition comprising:
a cyclic siloxane selected from the group consisting of cyclotetrasiloxane (octamethylcyclotetrasiloxane), cyclopentasiloxane (decamethylcyclopentasiloxane), cyclohexasiloxane (dodecamethylcyclohexasiloxane), and mixtures thereof;
a poly(dimethylsiloxane) having a viscosity between 100 cSt and 350 cSt;
a silicone gel in the form of a dispersion of a silicone elastomer in a silicone oil, wherein the silicone elastomer is selected from the group consisting of polysilicone-11, cetearyl dimethicone/vinyl dimethicone crosspolymer, dimethicone/phenyl vinyl dimethicone crosspolymer, and dimethicone/vinyl dimethicone crosspolymer, and wherein the silicone oil is selected from the group consisting of phenyl trimethicone and phenyl dimethicone;
a polymethylsilsesquioxane powder; and
a tetra($C_8$-$C_{24}$ acyl)ascorbic acid ester or salt thereof;
wherein
the concentration of the cyclic siloxane is between 55% and 65% by weight of the composition;
the concentration of the poly(dimethylsiloxane) is between 3% and 7% by weight of the composition; and
the concentration of the silicone gel is between 30% and 40% by weight of the composition.

2. The method of claim 1, wherein the poly(dimethylsiloxane) has a viscosity of 200 cSt.

3. The method of claim 1, wherein the cyclic siloxane is cyclopentasiloxane.

4. The method of claim 3, wherein the silicone elastomer is polysilicone-11 and the silicone oil is phenyl trimethicone.

5. The method of claim 4, wherein the poly(dimethylsiloxane) has a viscosity of 200 cSt.

6. The method of claim 1, wherein the concentration of ascorbic acid tetraisopalmitate is between 0.3% and 0.7% by weight of the composition.

7. A method for the treatment of wounds to reduce scarring comprising administering to a patient in need thereof an effective amount of a composition comprising:
cyclopentasiloxane;
a poly(dimethylsiloxane) having a viscosity between 100 cSt and 350 cSt;
a silicone gel in the form of a dispersion of a silicone elastomer in a silicone oil, wherein the silicone elastomer is polysilicone-11 and the silicone oil is phenyl trimethicone;
a polymethylsilsesquioxane powder; and
a tetra($C_8$-$C_{24}$ acyl)ascorbic acid ester or salt thereof;
wherein
the concentration of cyclopentasiloxane is between 55% and 65% by weight of the composition;
the concentration of the poly(dimethylsiloxane) is between 2% and 10% by weight of the composition;
the concentration of the silicone gel is between 30% and 40% by weight of the composition; and
the concentration of ascorbic acid tetraisopalmitate is between 0.1% and 2% by weight of the composition.

8. The method of claim 7, wherein the polymethylsilsesquioxane powder has an average particle size of 4-8 micrometers.

9. The method of claim 7, wherein the concentration of the polymethylsilsesquioxane powder is between 1% and 5% by weight of the composition.

10. The method of claim 8, wherein the concentration of the polymethylsilsesquioxane powder is between 2% and 3% by weight of the composition.

11. The method of claim 8, wherein the concentration of the poly(dimethylsiloxane) is between 3% and 7% by weight of the composition.

12. The method of claim 10, wherein the concentration of the poly(dimethylsiloxane) is between 3% and 7% by weight of the composition.

13. The method of claim 12, wherein the poly(dimethylsiloxane) has a viscosity of 200 cSt.

14. The method of claim 10, wherein the concentration of ascorbic acid tetraisopalmitate is between 0.3% and 0.7% by weight of the composition.

15. The method of claim 12, wherein the concentration of ascorbic acid tetraisopalmitate is between 0.3% and 0.7% by weight of the composition.

16. The method of claim 1, wherein the tetra($C_8$-$C_{24}$ acyl) ascorbic acid ester or salt thereof is ascorbic acid tetraisopalmitate.

17. The method of claim 7, wherein the tetra($C_8$-$C_{24}$ acyl) ascorbic acid ester or salt thereof is ascorbic acid tetraisopalmitate.

* * * * *